US007622622B1

(12) United States Patent
Woodle et al.

(10) Patent No.: US 7,622,622 B1
(45) Date of Patent: Nov. 24, 2009

(54) PROCESS FOR THE HIGH YIELD PRODUCTION OF MONOALKYLAROMATICS

(75) Inventors: Guy B. Woodle, Mount Prospect, IL (US); Robert J. Schmidt, Barrington, IL (US); Deng-Yang Jan, Elk Grove Village, IL (US); James A. Johnson, Clarendon Hills, IL (US); Elena Z. Maurukas, Lemont, IL (US); Raelynn M. Miller, LaGrange, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 10/872,615

(22) Filed: Jun. 21, 2004

(51) Int. Cl.
*C07C 2/66* (2006.01)
(52) U.S. Cl. .................................................. 585/467
(58) Field of Classification Search ................. 585/446, 585/467
See application file for complete search history.

(56) References Cited

U.S. PATENT DOCUMENTS

| | | | |
|---|---|---|---|
| 4,185,040 A | 1/1980 | Ward et al. ................. 585/467 |
| 4,774,377 A | 9/1988 | Barger et al. ................ 585/323 |
| 4,891,458 A | 1/1990 | Innes et al. ................. 585/323 |
| 5,030,786 A | 7/1991 | Shamshoum et al. ........ 585/467 |
| 5,086,193 A | 2/1992 | Sy ............................ 585/446 |
| 5,113,031 A | 5/1992 | Sy ............................ 585/467 |
| 5,215,725 A | 6/1993 | Sy ............................ 422/212 |
| 5,446,223 A | 8/1995 | Smith, Jr. ................... 585/313 |
| 5,723,710 A | 3/1998 | Gajda et al. ................. 585/467 |
| 5,756,873 A | 5/1998 | Ou ............................ 585/467 |
| 6,166,281 A * | 12/2000 | Anantaneni ................. 585/449 |
| 2004/0167371 A1 | 8/2004 | Pohl .......................... 585/449 |

OTHER PUBLICATIONS

U.S. Appl. No. 10/395,466, filed Mar. 21, 2003, Rohde et al.
U.S. Appl. No. 10/395,624, filed Mar. 21, 2003, Jan et al.

* cited by examiner

*Primary Examiner*—Thuan Dinh Thuan
(74) *Attorney, Agent, or Firm*—David J. Piasecki

(57) ABSTRACT

Disclosed is a process and apparatus for alkylating light olefin with benzene at near but less than full conversion of the olefin. We have found that stopping below full conversion of the olefin maximizes yield of monoalkylbenzene.

13 Claims, 10 Drawing Sheets

US 7,622,622 B1

PROCESS FOR THE HIGH YIELD PRODUCTION OF MONOALKYLAROMATICS

FIELD OF THE INVENTION

This invention relates to a process for alkylating olefins and aromatics to produce monoalkylaromatics. More particularly, this invention relates to the production of monoalkylaromatics with less than full conversion of olefin to minimize production of polyalkylaromatics.

BACKGROUND OF THE INVENTION

The alkylation of aromatics with olefins to produce monoalkylaromatics is a well developed art which is practiced commercially in large industrial units. One commercial application of this process is the alkylation of benzene with ethylene to produce ethylbenzene which may be subsequently used to produce styrene. Another application is the alkylation of benzene with propylene to form cumene (isopropylbenzene) which is subsequently used in the production of phenol and acetone. Ethyltoluene and xylene are also important alkylation products.

Often the feedstock to such an aromatic conversion process will include an aromatic component or alkylation substrate, such as benzene, and a $C_2$ to $C_5$ olefin alkylating agent. In the alkylation zone, the aromatic feed stream and the olefinic feed stream are reacted over an alkylation catalyst to produce alkylated benzene. Polyalkylated benzenes are separated from monoalkylated benzene product and recycled to a transalkylation zone and contacted with benzene over a transalkylation catalyst to yield monoalkylated benzenes.

The catalysts for such alkylation or transalkylation reactions generally comprise zeolitic molecular sieves. U.S. Pat. No. 4,891,458 discloses the presence of a catalyst comprising zeolite beta. U.S. Pat. No. 5,030,786 discloses an aromatic conversion process employing zeolite Y, zeolite omega and zeolite beta molecular sieve catalyst. U.S. Pat. No. 4,185,040 discloses the alkylation of benzene to produce ethylbenzene or cumene employing zeolites such as molecular sieves of the X, Y, L, B, ZSM-5 and Omega crystal types. U.S. Pat. No. 4,774,377 discloses an aromatic conversion process involving alkylation over a catalyst comprising a solid phosphoric acid component followed by transalkylation using aluminosilicate molecular sieve transalkylation catalysts including X, Y, ultrastable Y, L, Omega, and mordenite zeolites.

Typical commercial alkylaromatic production processes are designed and operated to achieve an overall olefin conversion of 100%. U.S. Pat. No. 5,215,725; U.S. Pat. No. 5,113,031 and U.S. Pat. No. 5,086,193 describe catalytic packed bed distillation columns that provide essentially complete conversion of olefin. U.S. Pat. No. 5,446,223 describes a catalytic distillation column that can achieve about 90% olefin conversion but which must then be followed by a finishing reactor to convert the remaining olefin to product. The primary motivation for complete olefin conversion is efficient use of the olefinic feed which accounts for a substantial portion of the cost of production for these processes. Moreover, the monoalkylbenzene selectivity is directly related to benzene-to-olefin ratio and is limited by chemical equilibrium. U.S. Pat. No. 5,756,873 contends that olefins may oligomerize over the solid acid catalyst to form heavier compounds that may block acid sites and deactivate the catalyst. Consequently, stoichiometric excess of aromatics relative to olefins in the reactor feed has been employed to prevent deactivation and improve selectivity.

Current industrial practice requires measures be taken to prevent olefin breakthrough from the reaction zone. Loading double, triple and even quadruple the volume of catalyst necessary to alkylate all of the olefins prevents olefin breakthrough even as catalyst deactivates while prolonging the interval between fresh catalyst loadings or regeneration. Moreover, reaction temperatures must be increased as the catalyst deactivates to maintain olefin conversion and prevent olefin breakthrough. Additionally, stoichiometric excess of benzene to olefin requires additional utility cost to fractionate the benzene for recycle.

An object of the invention is to provide an alkylation process that maximizes monoalkylate production while minimizing polyalkylate production.

A further object of the invention is to provide an alkylation process that requires smaller catalyst volume and utility cost.

SUMMARY OF THE INVENTION

We have found that by limiting olefin conversion to be less than complete in the alkylation reaction section of an alkylaromatic production process, the monoalkylaromatic yield and selectivity can be increased by 5 to 15 mol-%. These advantages can be obtained even when olefin conversion is maintained above 92%. This increase in monoalkylate yield and selectivity provides an option to increase capacity of existing plants by operating at lower aromatic-to-olefin ratios or reduce the capital cost of new plant designs by taking advantage of the lower polyalkylate formation and aromatic recycle. Additionally, the catalyst volume in the reactor may be reduced because preventing olefin breakthrough is no longer an objective. The unconverted olefin may be recovered and recycled within the process to avoid substantial increases in olefin feed consumption and cost of production.

DETAILED DESCRIPTION OF THE INVENTION

Figure 1:
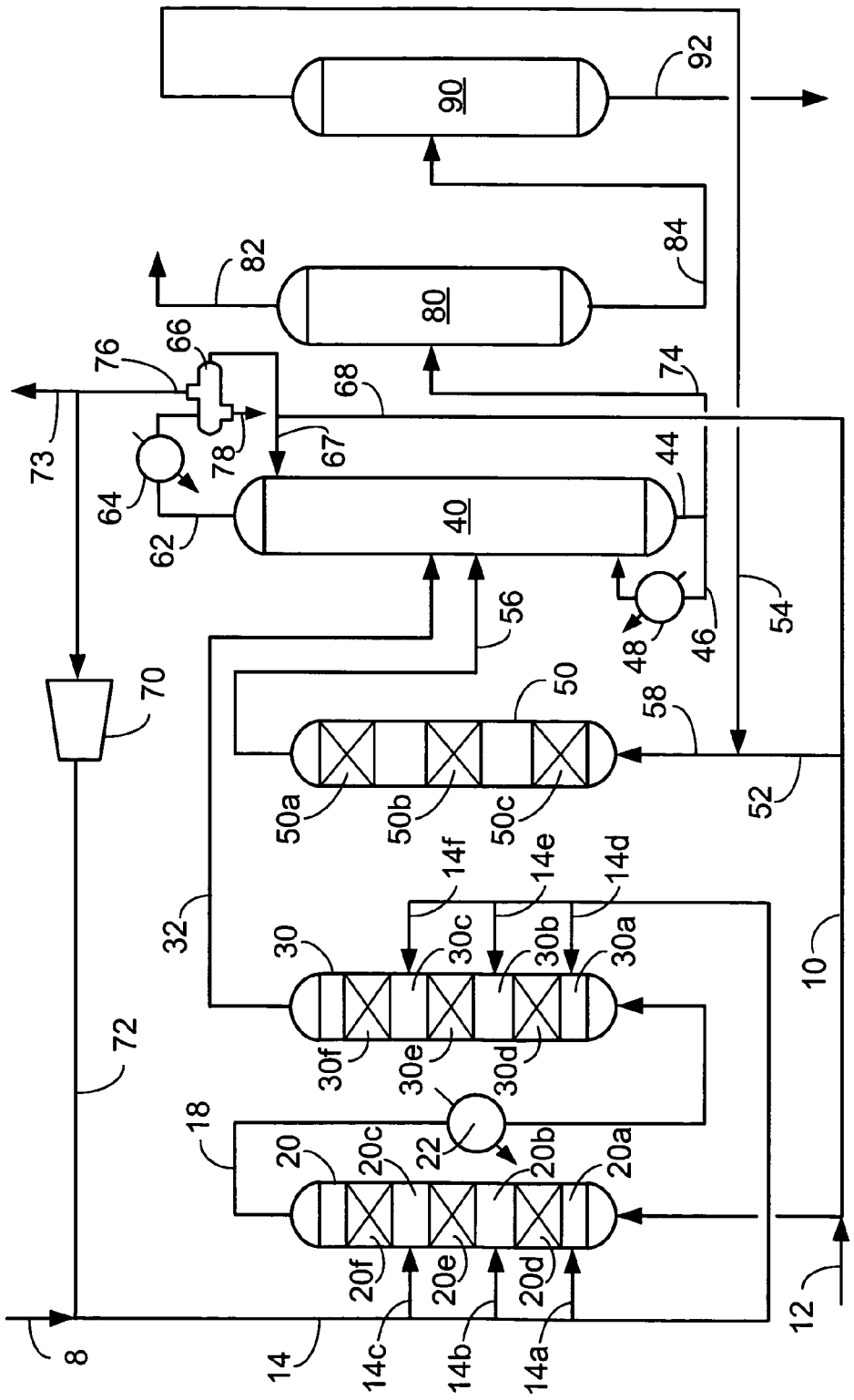
FIG. 1 depicts a flow scheme of the present invention for the production of ethylbenzene.

The aromatic feed stream of this invention comprising the alkylation substrate is generally a liquid and may contain water up to and beyond saturation conditions. Benzene is by far the most important representative of the alkylatable aromatic compounds which may be used as an alkylation substrate in the practice of the invention. An aromatic feed stream may comprise from about 5 to 99.9 mol-% benzene and may include a recycle stream from a styrene monomer production plant if ethylbenzene is the product. More generally, the aromatic compounds may be selected from the group consisting of benzene, naphthalene, anthracene, phenanthrene, and substituted derivatives thereof. The most important class of substituents found on the aromatic nucleus of alkylatable aromatic compounds are alkyl moieties. Although unsubstituted and monosubstituted benzenes, naphthalenes, anthracenes, and phenanthrenes are most often used in the practice of this invention, polysubstituted aromatics also may be employed.

The alkylation agent of the present invention is provided in an olefinic feed stream. The olefins may contain from 2 to 5 carbon atoms, and may be branched or linear olefins, either terminal or internal olefins. Alkylation reactions are conducted under at least partially liquid phase conditions, a criterion readily achieved for the lower olefins by adjusting reaction pressures. Among the lower olefins, ethylene and propylene are the most important representatives. An olefinic feed stream comprising an alkylation agent may include ethylene and/or propylene. An olefinic feed stream comprising propylene will typically be at least 50 wt-% pure with the balance including a large proportion of propane, with some propylene feeds being over 99 wt-% pure. Ethylene feeds will typically be over 80 wt-% pure. Alkylation agents may also be provided by alkyl constituents of a polyalkylbenzene in a transalkylation reaction zone. Diethylbenzene, triethylbenzene and diisopropylbenzene are prominent examples of polyalkylbenzenes that can provide such alkylation agents.

A wide variety of catalysts can be used in the alkylation reaction zone. The preferred catalyst for use in this invention is a zeolitic catalyst. The catalyst of this invention will usually be used in combination with a refractory inorganic oxide binder. Preferred binders are alumina or silica. Suitable zeolites include zeolite beta, ZSM-5, PSH-3, MCM-22, MCM-36, MCM-49, and MCM-56. Zeolite beta is described in U.S. Pat. No. 5,723,710. Preferred alkylation catalysts are a type Y zeolite having an alumina or silica binder or a beta zeolite having an alumina or silica binder. The zeolite will be present in an amount between about 5 wt-% and about 90 wt-% of the catalyst and preferably between about 10 wt-% and about 70 wt-% of the catalyst depending on the specific application. We have also found that UZM-8, a zeolitic material described in U.S. patent application Ser. No. 10/395,466, which is incorporated herein by reference, may serve as an alkylation catalyst that provides high monoalkylbenzene yield.

The conditions under which the alkylation reaction is conducted are set to achieve high but not complete conversion of the olefinic alkylation agent. It is preferable to have olefin conversion of at least 95% relative to the feed, however, the advantages of the invention may be realized with an olefin conversion of at least 92%. The smaller the olefin conversion level of the present invention, the more unconverted olefin must be managed or recycled. Hence, it is desirable to keep olefin conversion as high as possible without losing monoalkylate aromatic yield. However, less than maximum monoalkylate aromatic yield advantages of this invention may still be obtained by conceding monalkylate aromatic yield to boost olefin conversion and still staying short of full olefin conversion. Data showed that monoalkylate aromatic yield at 99.9% olefin conversion was in some cases far superior to monoalkylate aromatic yield relatively nearer to 100% olefin conversion. Olefin conversion in the context of the present invention refers to a targeted conversion level for a sustained period of time instead of a momentary conversion level achieved only while progressing or adjusting to a targeted olefin conversion level. Moreover, olefin conversion in the context of the present invention also refers to a condition of a fully active alkylation catalyst bed as opposed to a catalyst bed that is approaching or experiencing deactivation. Reduced conversion of the olefinic alkylation agent can be achieved by increasing space velocity and by reducing temperature. Space velocity is reduced by loading less catalyst into the alkylation reactor. Hence, a way to practice the present invention may exclude the loading of excess catalyst to increase catalyst life. Instead, periodical catalyst washing may be necessary to restore catalytic activity. Catalyst may be periodically reactivated by washing the catalyst with fresh benzene. Once catalyst is loaded, space velocity can be adjusted by varying the feed rate of olefin. Varying olefin feed rate may also be accompanied by a relational change in benzene feed rate, for example, to maintain a constant benzene-to-olefin ratio if desired. Particular conditions will depend upon the aromatic compound and the olefin used.

Since the alkylation reaction is conducted under at least partially liquid phase conditions, reaction pressure is adjusted to maintain the olefin at least partially in the liquid phase. For ethylene, this means dissolving gaseous ethylene into the liquid benzene stream. Heavier olefins will liquefy. Pressures can vary within a wide range of about 101 kPa gauge to about 13172 kPa gauge (14.7 to 1910.5 psig). As a practical matter the pressure normally is in the range between about 689 kPa gauge and about 6895 kPa gauge (100 to 1000 psig) but usually is in a range between about 1379 and 4137 kPa gauge (200 and 600 psig). Pressure is not a critical variable and needs to be sufficient only to maintain at least partial liquid phase conditions. Representative alkylation temperatures include a range of between 170° and 270° C. for alkylation of benzene with ethylene and temperatures of 90° to 220° C. for the alkylation of benzene with propylene. The temperature range appropriate for alkylation of the alkylatable aromatic compounds of our invention with the olefins in the $C_2$ to $C_5$ range is between about 60° and about 400° C., with the most usual temperature range being between about 90° and 270° C. Reactants generally pass through the alkylation zone at a mass flow rate sufficient to yield a weight hourly space velocity based on the olefin feed from 0.1 to 100 $hr^{-1}$ and especially from about 0.2 to 30 $hr^{-1}$.

The ratio of alkylatable aromatic compound to olefin used in the process of the invention will depend upon the degree of selective alkylation desired as well as the relative costs of the aromatic and olefinic components of the reaction mixture. The monoalkylate benzene selectivity is directly related to the benzene-to-olefin ratio. Consequently, the composition of the effluent stream from the alkylation reactor will be affected by the benzene-to-olefin ratio. For alkylation of benzene by propylene and ethylene, benzene-to-olefin molar ratios may be as low as about 1.0 and as high as about 20.0, with a ratio of 1.5 to 8.0 being suitable and 1.5 to 3.5 being preferred.

In the production of cumene with a benzene alkylation substrate and a propylene alkylating agent, the propylene-containing stream will typically also contain propane. The propylene stream may contain from 0 to 50 wt-% propane, and typically, the propylene stream contains from 0.5 to 35 wt-% propane. In the production of ethylbenzene with a benzene alkylation substrate and an ethylene alkylating agent, the ethylene-containing stream will typically be over 80 wt-% pure with the balance being mostly ethane.

The alkylation reaction zone will often provide a wide variety of undesired by-products. For example, in the alkylation of benzene with ethylene to produce ethylbenzene, the reaction zone can also produce di- and triethylbenzene in addition to other ethylene condensation products. Similarly, in the alkylation of benzene with propylene to produce cumene, the reaction zone can produce di- and triisopropylbenzene in addition to still more condensation products. These polyalkylated aromatics contact additional aromatic substrate in a transalkylation reactor to produce additional monoalkylated product. The transalkylation reaction zone may typically use a zeolitic catalyst. In most cases the zeolitic catalyst includes an inorganic oxide binder. The preferred inorganic oxide for use in the transalkylation catalyst is alumina with gamma-alumina, eta-aluminum and mixtures thereof being particularly preferred. The zeolite may be present in a range of from 5 to 99 wt-% of the catalyst and the refractory inorganic oxide may be present in a range of from 1 to 95 wt-%. Preferred transalkylation catalysts are a type Y zeolite having an alumina or silica binder or a beta zeolite having an alumina or silica binder.

There is no requirement that the alkylation reaction zone and the transalkylation reaction zone use the same catalyst. This process is useful for any arrangement of alkylation reaction zone and transalkylation reaction. However, it has been found that a beta zeolite or a Y type zeolite contained in an alumina binder will perform very well when used in both the alkylation reaction zone and the transalkylation reaction zone. Therefore, in the preferred embodiment of this invention, in the cumene context, both reaction zones will use the same catalyst, beta zeolite. Whereas, in the case of ethylbenzene, the alkylation and transalkylation zones will preferably use beta zeolite and Y-type zeolite, respectively. UZM-8 catalyst may also be a preferred alkylation catalyst. Additionally, transalkylation reactions occur in an alkylation reaction zone and alkylation reactions occur in a transalkylation reaction zone, both zones may be referred to as alkylation zones.

The transalkylation reaction can be carried out in a broad range of operating conditions that include a temperature of from 100° to 390° C. (212° to 734° F.) and pressure ranging from 101 to about 13171 kPa gauge (14.7 to 1910 psia). The pressure is generally selected so that the reactants will remain in the liquid phase. Accordingly, preferred pressures for the transalkylation reaction zone range from 1013 to about 5066 kPa gauge (147 to 734 psia). A weight hourly space velocity based on polyalkylated aromatic species to be transalkylated of from 0.1 to 100 hr$^{-1}$ is desirable for the transalkylation reaction zone with LHSV of from 0.5 to 50 hr$^{-1}$ being preferred. The composition of the effluent stream leaving the transalkylation reactor will be affected by a phenyl group-to-alkyl group ratio under which the reactor is operated. Preferably the phenyl group-to-alkyl group ratio will be between about 1.0 and about 10.

The transalkylation and alkylation reaction zones may be operated and arranged in any manner that provides the desired operating temperatures and number of contacting stages. Multiple contacting stages in the alkylation zone are routinely used to provide cooling by staged addition of reactants to multiple beds of alkylation catalyst. The multiple injection of the reactants serves to cool the stages between alkylation catalyst beds and provide temperature control. The alkylation catalyst is ordinarily arranged in multiple beds to permit interbed injection of alkylating agent. The separate alkylation catalyst beds may be arranged in a single vessel or in multiple vessels. This invention can be used with a traditional parallel arrangement for the alkylation zone and the transalkylation zone where feed streams are sent independently to each reaction zone and the effluent separately recovered. Alternatively, the reaction zone may have a series flow arrangement with the effluent from the transalkylation zone cascading to the alkylation zone along with additional benzene or vice versa. In the alkylation zone, a large excess of benzene may pass through a series of alkylation catalyst beds with interstage injection of alkylating agent and any additional quantities of benzene. Alkylation reactor effluent recycle may also be used advantageously to quench individual catalyst beds for further improvement in temperature control without the need for additional consumption of fresh benzene. In the series flow arrangement a common vessel may contain a transalkylation reaction zone and one or more alkylation reaction zones. For very large units, separate vessels for the transalkylation catalyst bed and one or more of the alkylation catalyst beds may be more advantageous.

A separation zone will be used to recycle benzene and polyalkylbenzene to the process and recover monoalkylate product. An overhead condenser on at least one fractionation column in a separation zone may be used for the separation of water from an overhead stream and the return of a portion of the aromatic hydrocarbon condensate to the column as reflux. An additional separation column may be necessary to remove substantial impurities that accompany the alkylation agent feed, such as is typically the case with propylene. Pressures in the separator columns will be less than in the alkylation and transalkylation zones because vaporization of olefin is the objective in the former to separate the olefin from the alkylbenzene. However, in an embodiment in which a catalytic distillation alkylation reactor is used, the pressure differential between reaction zone and the separation zone may be relatively small.

Because a substantial amount of olefinic alkylation agent is unconverted in the alkylation reactor to boost monoalkylate yield, an olefin recycle unit is necessary to make use of the unconverted olefin. Otherwise, up to 8 mol-% of olefinic alkylation agent in the feed will be lost. The olefin recycle unit can be a finishing reactor downstream of the alkylation reactor or be a recycle device downstream of the alkylation reactor which recycles upstream to the alkylation reactor.

DETAILED DESCRIPTION OF THE DRAWINGS

The further description of embodiments of the process and apparatus of this invention is presented with reference to the attached Figures. The Figures represent aspects of embodiments of the invention and are not intended to be a limitation on the generally broad scope of the invention as set forth in the claims. Of necessity, some miscellaneous appurtenances including valves, pumps, separators, receivers, heat exchangers, etc. have been omitted from the drawings. Only those vessels and lines necessary for a clear and complete understanding of the process and apparatus of the present invention are illustrated. In all cases, the process is a continuous process.

FIG. 1 illustrates an embodiment of this is invention for the production of ethylbenzene. A stream comprising ethylene enters the process in a line 8 and is added to line 14 from which it is injected into first and second alkylation reactors 20, 30, respectively. The ethylene stream is typically at least about 80 wt-% pure with the remainder mostly being ethane. Preferably, the ethylene stream is 99.5 wt-% pure. Alkylation reactors are shown as upflow reactors, but downflow reactors may also be suitable. Ethylene is injected into the alkylation reactors 20, 30 in several lines 14a-f into pre-bed spaces 20a-c, 30a-c prior to entry into catalyst beds 20d-f, 30d-f. The catalyst beds 20d-f, 30d-f contain alkylation catalyst to alkylate benzene and ethylene to produce ethylbenzene. Fresh feed benzene is added from a line 12 to the process into a line 10. Benzene in line 10 is fed to the first alkylation reactor 20 where it initially mixes with ethylene from the line 14a in the pre-bed space 20a and enters the catalyst bed 20d. The effluent from the catalyst bed 20d is mixed with fresh ethylene from the line 14b in the pre-bed space 20b and enters into the catalyst bed 20e. The process is repeated for the number of beds in the first alkylation reactor 20. Although three catalyst beds are shown in the alkylation reactors 20, 30, more or less may be suitable. Intermediate alkylation effluent from the first alkylation reactor 20 is transported in a line 18 to the second alkylation reactor 30. A heat exchanger 22 cools the effluent in the line 18 to a desirable alkylation temperature before it is delivered to the pre-bed space 30a. Ethylene injected into the pre-bed space 30a from the line 14d mixes with the intermediate alkylation effluent from the line 18 and enters the catalyst bed 30d. The same process is repeated for the catalyst beds 30e and 30f and the alkylation reactor effluent from the second alkylation reactor 30 is transported to a benzene column 40 in a line 32. The alkylation reactor effluent stream may be depressured by passing through a pressure control valve which is not shown, may be heated or cooled in a heater or heat exchanger which is also not shown, or both. Additionally, more or less alkylation reactors may be suitable. The alkylation reactors are operated under conditions that assure at least about 92% and preferably at least about 95% of the ethylene is converted, but less than full conversion. Preferably, no more than 99.9% of the ethylene is converted in alkylation reactors 20, 30.

Benzene from the line 10 is routed to the transalkylation reactor 50 through a line 52. A line 54 carries a polyethylbenzene PEB) column overhead stream of diethylbenzene (DEB) and triethylbenzene (TEB) from the overhead of a PEB column 90 to mix with the benzene in the line 52 to provide a transalkylation feed in a line 58. The transalkylation reactor 50 contains three catalyst beds 50a-50c of transalkylation catalyst. More or less catalyst beds may be used in the transalkylation reactor 50. The transalkylation catalyst promotes transalkylation reactions wherein ethyl groups from the DEB and TEB are transalkylated with benzene to produce ethylbenzene. Hence, a transalkylation effluent stream in line 56 from the transalkylation reactor 50 contains a greater concentration of ethylbenzene and a lower concentration of DEB and TEB than in the transalkylation feed in line 58.

As shown in FIG. 1 with the alkylation and transalkylation reactors in parallel, two different streams are fed to the benzene column 40. The alkylation reactor effluent stream in the line 32 feeds up to 8 mol-% ethylene relative to the feed, some inert lights, traces of water, benzene, ethylbenzene, DEB, TEB and few heavier PEB's to the benzene column 40. The transalkylation effluent stream in the line 56 feeds benzene, ethylbenzene, DEB and TEB and few heavier PEBs to the benzene column 40. If it were desired to run the transalkylation reactor 50 and the alkylation reactors 20, 30 in series, the effluent from the transalkylation reactor 50 would be transported to the alkylation reactor 20 through line 10 instead of being transported to the benzene column 40. In the benzene column 40, the ethylene is separated from the ethylbenzene and heavier components. A benzene column overhead stream comprising benzene and ethylene exits the benzene column through a line 62 and enters a condenser 64 where it is cooled to a temperature between about 120° and about 170° C. The condensed overhead enters a receiver 66 which includes a trap for dispensing undissolved or free water in a line 78 and ethylene and light gases in a line 76. A portion of the overhead hydrocarbon stream comprising mostly benzene is refluxed to the benzene column 40 via line 67 while the remaining benzene in line 68 is transported to the transalkylation reactor 50 via line 52 and to alkylation reactors 20, 30 via line 10. A benzene column bottom stream comprising the product ethylbenzene and the by-products including PEBs exits the benzene column in a line 44. A reflux stream in line 46 is heated in reboiler 48 and refluxed to the benzene column 40. Line 74 carries a benzene column bottoms stream to an ethylbenzene column 80. The ethylene in line 76 is routed through an olefin recycle unit comprising a compressor 70 to compress the gaseous ethylene to a pressure at which it will dissolve into the liquid benzene in the alkylation reactors 20, 30 operating under at least partial liquid phase. Pressurized ethylene is transported from the compressor 70 via line 72 and line 14 to the alkylation reactors 20, 30. The compressor may pressurize the ethylene stream just above a pressure at which it will be admitted into line 14. A vent line 73 may be used to purge inerts such as ethane from the system.

The ethylbenzene column 80 separates the benzene column bottom stream from the line 74 by distillation into two streams. An ethylbenzene column overhead stream comprising the product ethylbenzene exits the ethylbenzene column 80 in a line 82 is recovered from the process. An ethylbenzene column bottom stream comprises by-product PEBs, typically including DEBs, TEBs and heavier PEBs such as butylbenzenes, dibutylbenzenes, tributylbenzenes, ethylbutylbenzenes, diethylbutylbenzenes, and diphenylethane. The ethylbenzene column bottom stream exits the ethylbenzene column 80 in a line 84, and passes to the PEB column 90.

The PEB column 90 separates the ethylbenzene column bottom stream in the line 84 into two streams. A PEB column bottom stream comprising PEBs heavier than TEB exits from the bottom of the PEB column 90 in a line 92 and is rejected from the process. The PEB column overhead stream comprising DEBs and TEBs exits the PEB column 90 in the line 54 and recycles to be mixed with the benzene feed to the transalkylation reactor 50 in the line 52 as described previously. In some cases, all or part of tetraethylbenzenes (TeEBs) may be recovered in the overhead stream in line 54 along with DEBs and TEBs and recycled to the transalkylation reactor 50. Overhead and bottom receivers and heat exchangers are not shown for the ethylbenzene column 80 and the polyethylbenzene column 90.

Figure 2:
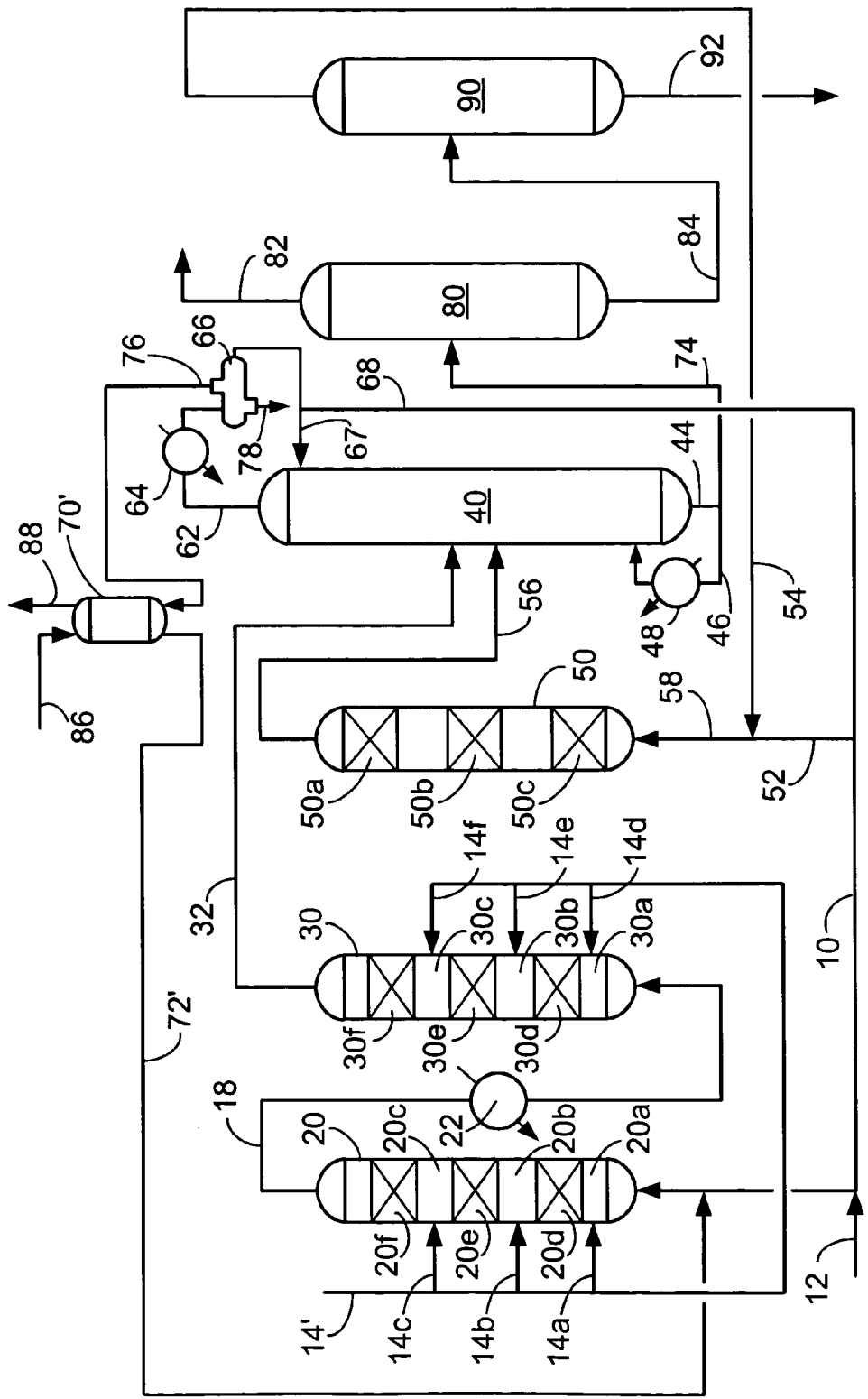
FIG. 2 depicts an alternative flow scheme of the present invention for the production of ethylbenzene.

FIG. 2 shows a process and apparatus that utilizes a recontact tower 70' as an olefin recycle device for recycling unconverted olefin. All of the reference numerals that designate an element in FIG. 2 which corresponds to a similar element in FIG. 1 but which has a different configuration will be marked with a prime symbol ('). Otherwise, the same reference numeral will designate corresponding elements in FIGS. 1 and 2 which have the same configuration. The difference between the configurations in FIGS. 1 and 2 primarily lies in that unconverted ethylene in line 76 is passed to a recontact tower 70'. The ethylene is preferably countercurrently contacted with benzene from line 86 over a series of trays to dissolve the bulk of the gaseous ethylene in the liquid benzene. The recontact tower may be operated at a pressure between about 689 and about 6895 kPa gauge (100 to 1000 psig) and a temperature between about 25 and about 125° C. The benzene stream saturated with ethylene leaves the contact tower 70' through line 72' and is admixed with benzene in line 10. Fresh ethylene is added to the process via line 14'. Ethylene not absorbed in the benzene stream in the contact tower 70' is vented in line 88 or perhaps recycled (not shown) to line 76 or line 14'. Recycling vented ethylene to line 14' may require a compressor to pressurize the ethylene, but a smaller compressor may be needed. The rest of the process and apparatus of FIG. 2 is the same as in FIG. 1.

Figure 3:
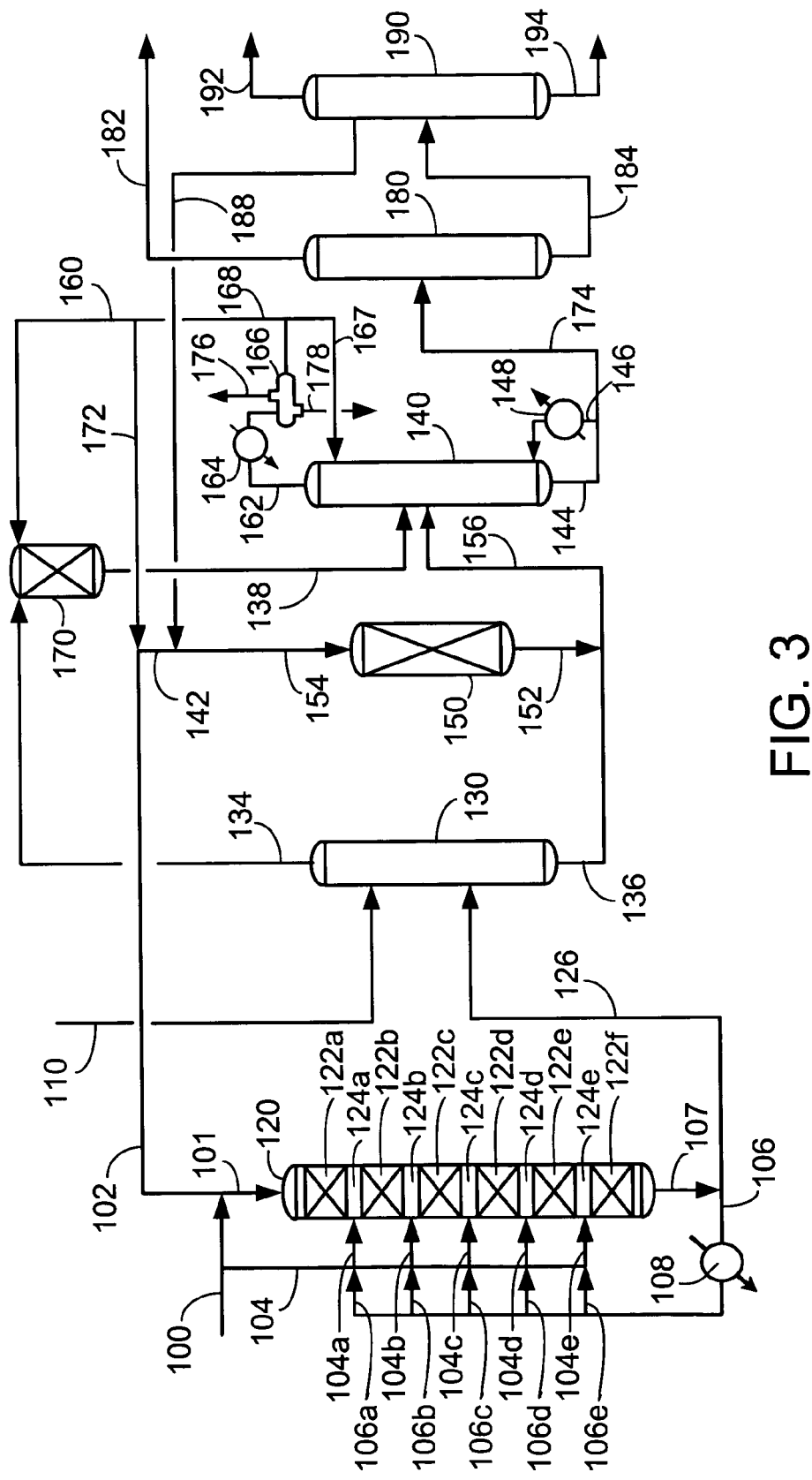
FIG. 3 depicts a flow scheme of the present invention for the production of cumene.

FIG. 3 depicts a flow scheme for an apparatus and process for producing cumene according to the present invention. A propylene stream in a line 100 typically containing 0.5 to 35 wt-% propane is mixed with a benzene stream in a line 102, and a line 101 introduces the mixture of benzene and propylene to a first catalyst bed 122a in an alkylation reactor 120.

The alkylation reactor 120 is shown to be a downflow reactor, but an upflow reactor may be suitable. The catalyst bed 122*a* includes an alkylation catalyst for the alkylation of propylene and benzene to produce cumene. The effluent from the catalyst bed 122*a* enters an interbed space 124*a*. Recycled alkylation effluent from a line 106 is cooled by a heat exchanger 108 and is recycled to the alkylation reactor 120 by distribution lines 106*a-e* and feed inlet lines 104*a-e*. Propylene in a line 104 diverted from the line 100 is distributed to the feed inlet lines 104*a-e* in which the propylene mixes with recycled alkylation effluent from the distribution lines 106*a-e*, respectively. The mixture of recycled alkylation effluent and propylene in the feed inlet lines 104*a-e* is delivered to the respective interbed spaces 124*a-e* in which it mixes with effluent from the preceding catalyst bed 122*a-e*, respectively, and enters the subsequent catalyst bed 122*b-f*, respectively. The alkylation effluent exits the last catalyst bed 122*f* in a line 107. A portion of the alkylation effluent is recycled by the line 106 to the alkylation reactor 120, while another portion is routed to a depropanizer column 130 in a line 126. The alkylation reactor effluent stream in the line 107 includes up to 8 mol-% propylene relative to the feed, some inert lights including propane, traces of water, benzene and cumene. If the propylene feed in line 100 has a sufficiently low concentration of propane, the depropanizer column 130 may be omitted and line 126 would carry alkylation effluent to the benzene column 140. Under this alternative, unconverted propylene would be separated from cumene in the benzene column 140 and then propylene would be separated from some of the benzene in the overhead section of the benzene column 140 as will be described.

Fresh feed benzene in a line 110 is delivered to the depropanizer column 130. If the fresh feed benzene is sufficiently dry, line 110 may deliver fresh feed benzene to line 102. The depropanizer column separates propylene and propane from cumene and heavier polyisopropylbenzene. The depropanizer column 130 distills propylene, propane and excess water in an overhead stream in an overhead line 134. The overhead line 134 is routed to an olefin recycle unit comprising a finishing reactor 170. The finishing reactor 170 contacts the propylene with benzene from a benzene column overhead stream diverted in line 160 over alkylation catalyst. The finishing reactor can operate at 100% conversion without concern for reduced cumene selectivity. The propylene flow rate will be relatively small. The consequently higher benzene to olefin ratio diminishes production of polyalkylbenzenes and any additional selectivity to polyalkylbenzenes will have a negligible impact on cumene selectivity in the total product. The same alkylation catalyst in the alkylation reactor 120 may be used in the finishing reactor 170. The finishing reactor 170 may be operated at a temperature in the range of about 90° C. and about 220° C. and a pressure in the range of about 689 kPa gauge and about 6895 kPa gauge (100 to 1000 psig). An effluent stream from the finishing reactor 170 comprising cumene, benzene and inerts including propane are delivered in line 138 to the benzene column 140. Alternatively, the depropanizer overhead line 134 could be routed to a transalkylation reactor 150 in which benzene feed and propylene could alkylate over a transalkylation catalyst. Hydrocarbons heavier than propane are withdrawn from the depropanizer column 130 through the depropanizer bottom stream in a line 136 and transported to the benzene column 140.

The depropanizer bottom stream in line 136 is mixed with transalkylation effluent in a line 152 and transported to the benzene column 140 in line 156. The effluent stream from the finishing reactor 170 in line 146 may mix with the stream in line 156 in route to the benzene column 140 or it may be delivered to the benzene column 140 separately. The benzene column 140 produces a benzene column overhead stream comprising benzene, propane and water in a line 162 and a benzene column bottom stream comprising cumene and polyisopropylbenzene in a line 144. In the benzene column 140, propylene is separated from cumene and heavier polyisopropylbenzenes if no depropanizer column 130 is used. The benzene column overhead stream exits the benzene column 140 through a line 162 and enters a condenser 164 where it is cooled to a temperature between about 120° and about 170° C. The condensed overhead enters a receiver 166 which includes a trap for dispensing undissolved or free water in a line 178 and any propane and light gases in a line 176. If no depropanizer column 130 is used, line 162 containing benzene, propylene and propane will be routed to the finishing reactor 170 without cooling in condenser 164 or venting from receiver 166 in an effort to maintain the propylene in benzene solution. In such an alternative, a provision such as a flash drum may be necessary to separate inert propane out of the effluent stream from the finishing reactor 170 in line 138. A portion of the overhead hydrocarbon stream comprising mostly benzene is refluxed to the benzene column 140 via line 167 while the remaining benzene in line 168 is split between line 160 that delivers benzene to the finishing reactor 170 and line 172 that delivers benzene to lines 102 and 142. The benzene in line 142 is mixed with an intermediate stream comprising diisopropylbenzene (DIPB) in a line 188 from a heavies column 190. The mixture of benzene and DIPB in a line 154 are delivered to the transalkylation reactor 150. The DIPB transalkylates with benzene over a transalkylation catalyst bed 156 in the transalkylation reactor 150 to produce cumene. Transalkylation effluent in the line 152 has a greater concentration of cumene and a smaller concentration of benzene and DIPB than in the line 154.

The benzene column bottom stream in the line 144 is split between a reflux line 146 that is heated in reboiler 148 and refluxed back to the benzene column and a benzene column bottom stream delivered by line 174 to a cumene column 180. The cumene column 180 provides a cumene overhead stream comprising product cumene which is recovered in a line 182. The cumene column bottoms stream in a line 184 comprising hydrocarbons heavier than cumene is delivered to the heavies column 190. The heavies column 190 produces an intermediate stream comprising DIPB in the intermediate line 188. Lighter material (containing for example cumenes and butylbenzenes) in the heavies overhead stream (containing for example diphenylpropane and heavy aromatic species) is withdrawn in an overhead line 192 and a heavies bottom stream is withdrawn in a bottom line 194.

Figure 4:
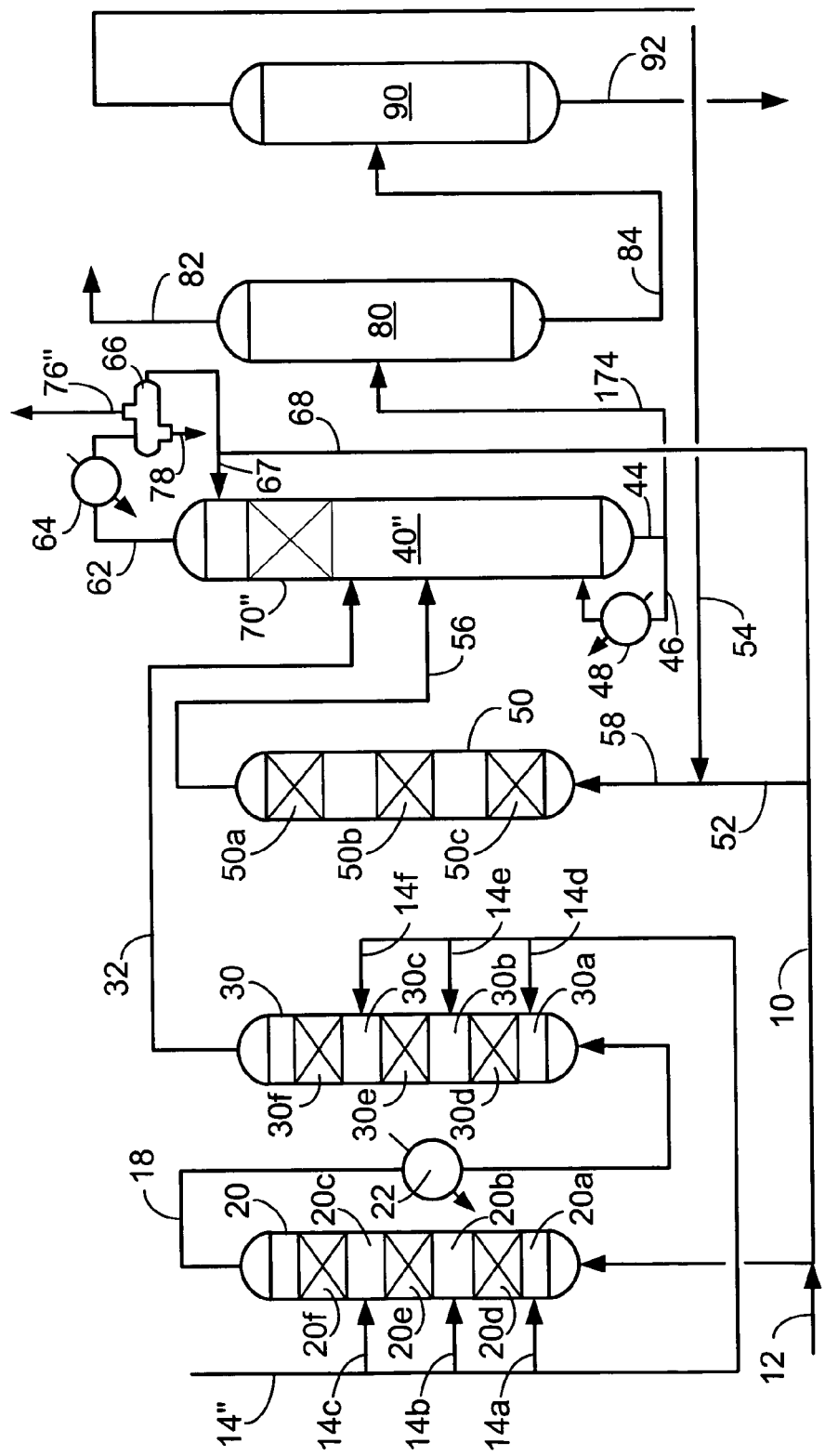
FIG. 4 depicts an alternative flow scheme of the present invention for the production of ethylbenzene.

FIG. 4 shows a flow scheme for making ethylbenzene similar to that in FIG. 1 except that the olefin recycle unit is a catalytic alkylation section 70" of the benzene column 40'. All of the reference numerals that designate an element in FIG. 4 which corresponds to a similar element in FIG. 1 or 2 but which has a different configuration will be marked with a double prime symbol ("). Otherwise, the same reference numeral will designate corresponding elements in FIGS. 1, 2 and 4 which have the same configuration.

A line 14" delivers ethylene to alkylation reactors 20, 30. No ethylene recycle line is necessary to recycle ethylene to line 14' because all of the ethylene unconverted in the alkylation reactors 20, 30 is fed by line 32 to the benzene column 40" that has an alkylation catalytic section 70" in an upper section thereof. The ethylene in benzene column 40" is separated from the ethylbenzene and polyethylbenzene. Benzene and ethylene move upwardly in the benzene column 40" to contact alkylation catalyst bed 70". The alkylation effluent in line 32 may enter the benzene column 40" closer to the catalyst bed 70" than the transalkylation effluent line 56 because essentially all of the olefin entering the benzene column 40" will enter in line 32. Preferably, the temperature and pressure at the feed point of line 32 and in the catalytic section 70" should be set to permit the ethylene and benzene to rise from the feed point to the catalytic section 70". The liquid phases of ethylene and benzene in the catalytic section 70" will react over the alkylation catalyst therein to yield ethylbenzene which will descend in the column 40". The temperature and pressure of the feed point of line 32 and the catalytic section 70" should be between about 60° C. and about 400° C. and between about 0 kPa gauge and about 2758 kPa gauge. The catalyst bed 70" can be supported in the benzene column 40" as is known in the art. Essentially all of the ethylene ascending in the benzene column 40" alkylates with benzene over the catalyst in bed 70" in the benzene column 40". The catalyst bed 70" will encounter a high benzene-to-ethylene ratio thus producing high ethylbenzene selectivity. In the overhead of the benzene column 40", ethane and gases are rejected in line 76", benzene is refluxed and recycled in lines 67 and 68, respectively, and water is rejected in line 78. Otherwise, the flow scheme of FIG. 4 operates substantially as in FIG. 1. A catalytic distillation section can also be applied to the alkylation of larger olefins, such as propylene, with benzene.

Figure 5:
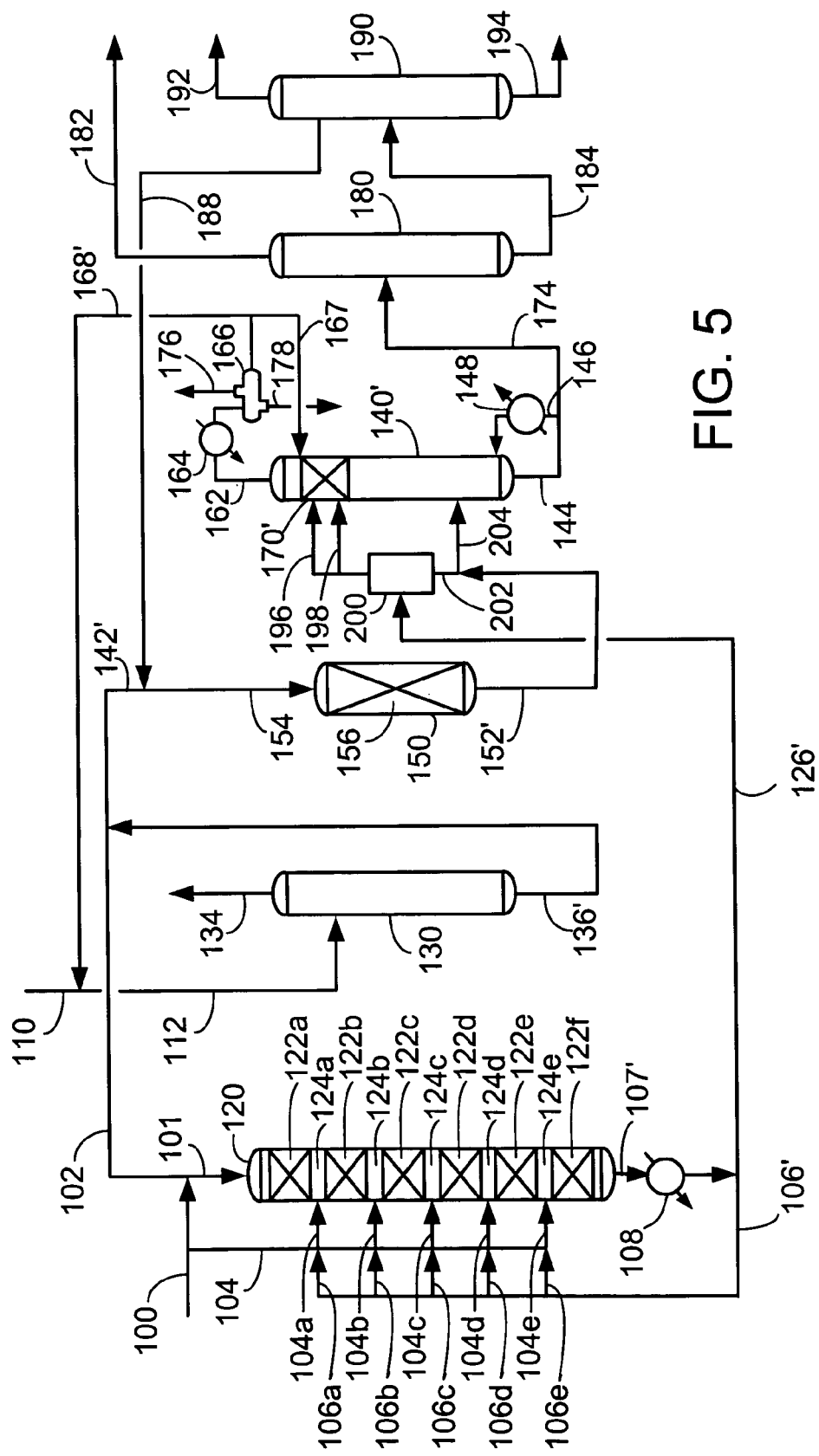
FIG. 5 depicts an alternative flow scheme of the present invention for the production of cumene.

FIG. 5 shows a flow scheme for making cumene similar to that in FIG. 3 but utilizing a catalytic distillation section 170" in the benzene column as the olefin recycle unit. All of the reference numerals that designate an element in FIG. 5 which corresponds to a similar element in FIG. 3 but which has a different configuration will be marked with a prime symbol ('). Otherwise, the same reference numeral will designate corresponding elements in FIGS. 3 and 5 which have the same configuration.

The alkylation reactor 120 has the same configuration as in FIG. 3. The alkylation reactor effluent stream in the line 107' includes up to 8 mol-% propylene relative to the feed, some inert lights including propane, traces of water, benzene and cumene. The stream 107' is cooled by cooler 108 and split. Line 106' recycles cooled alkylation reactor effluent back to the alkylation reactor 120 while line 126' carries cooled alkylation reactor effluent to a flash drum 200. The flash drum 200 roughly separates propylene and lights from cumene and heavier material. The flash drum may be run at a temperature between about 90° C. and about 200° C. and preferably between about 100° C. and about 170° C. The pressure of the flash drum may be set between about 0 kPa gauge (0 psig) and about 1000 kPa gauge (145 psig) and preferably no more than 700 kPa gauge (101 psig). The operating pressure of the flash drum 200 may be somewhat higher than the pressure in the benzene column 140' to allow for convenient introduction of the vapor and liquid feed streams to the benzene column 140' without additional compression or pumping. The pressure of the benzene column can vary but could be in the range of approximately 0 kPa gauge (0 psig) to about 2758 kPa gauge (400 psig) in the catalytic section 170'. The temperature of the catalytic section 170' in the benzene column 140' can vary but would be preferably be between 60° C. and about 400° C. Flashed propylene is directed by one or more lines 196, 198 to optimal locations of the catalytic section 170' in the benzene column 140'. Heavier components such as benzene, cumene and polyisopropylbenzene are removed from the flash drum 200 by line 202 and mixed with transalkylation effluent in line 152' and delivered by line 204 to a lower, preferably non-catalytic, section of the benzene column. Essentially all of the propylene alkylates with benzene in the catalytic section 170' to produce cumene. The catalytic section 170' can operate at 100% olefin conversion with a high benzene-to-propylene ratio without significantly impacting cumene selectivity because the propylene flow rate will be relatively small.

The benzene column 140' produces a benzene column overhead stream comprising benzene, propane and water in a line 162 and a benzene column bottom stream comprising cumene and polyisopropylbenzene in a line 144. In the flash drum 200, propylene is roughly separated from cumene and heavier polyisopropylbenzenes, and further separation is made in the benzene column 140'. The benzene column overhead stream exits the benzene column 140' through the line 162 and enters a condenser 164 where it is cooled to a temperature between about 120° and about 170° C. The condensed overhead enters a receiver 166 which includes a trap for dispensing undissolved or free water in a line 178 and propane and light gases in a line 176. A portion of the overhead hydrocarbon stream comprising benzene is refluxed to the benzene column 140' via line 167 while the remaining benzene in line 168' is recycled. Fresh feed benzene in line 110 is dried in depropanizer 130. However, if the fresh feed benzene is sufficiently dry, line 110 may deliver fresh feed benzene to benzene line 102. If the propylene feed in line 100 contains substantial propane, the benzene in line 168' will contain propane that must be processed in a depropanizer column 130. Line 168' joins line 110 in FIG. 5 and the combined stream 112 carries benzene and propane to the depropanizer column 130. If fresh feed benzene in line 110 is not dried in the depropanizer column 130, line 168' may carry benzene and propane directly to the depropanizer column 130. If the propylene feed in line 100 is sufficiently free of propane, the depropanizer column 130 may be omitted in which case line 168' may deliver benzene to line 102 for distribution to the alkylation reactor 120 and the transalkylation reactor 150. In the depropanizer column 130, water, propane and lights are removed in overhead line 134 and benzene is removed in line 136' and is split. A portion of the benzene split from line 136' is delivered by line 102' to the alkylation reactor 120 in line 101 after mixing with propylene in line 100. Another portion of the benzene split from line 136' is carried by line 142' and mixed with an intermediate stream comprising diisopropylbenzene (DIPB) in a line 188 from a heavies column 190. The mixture of benzene and DIPB in a line 154 is delivered to the transalkylation reactor 150. The DIPB transalkylates with benzene over a transalkylation catalyst bed 156 in the transalkylation reactor 150 to produce cumene. Transalkylation effluent in the line 152 has a greater concentration of cumene and a smaller concentration of benzene and DIPB than in the line 154. The cumene column 180 and the heavies column 190 operate the same as described in FIG. 3.

Figure 6:
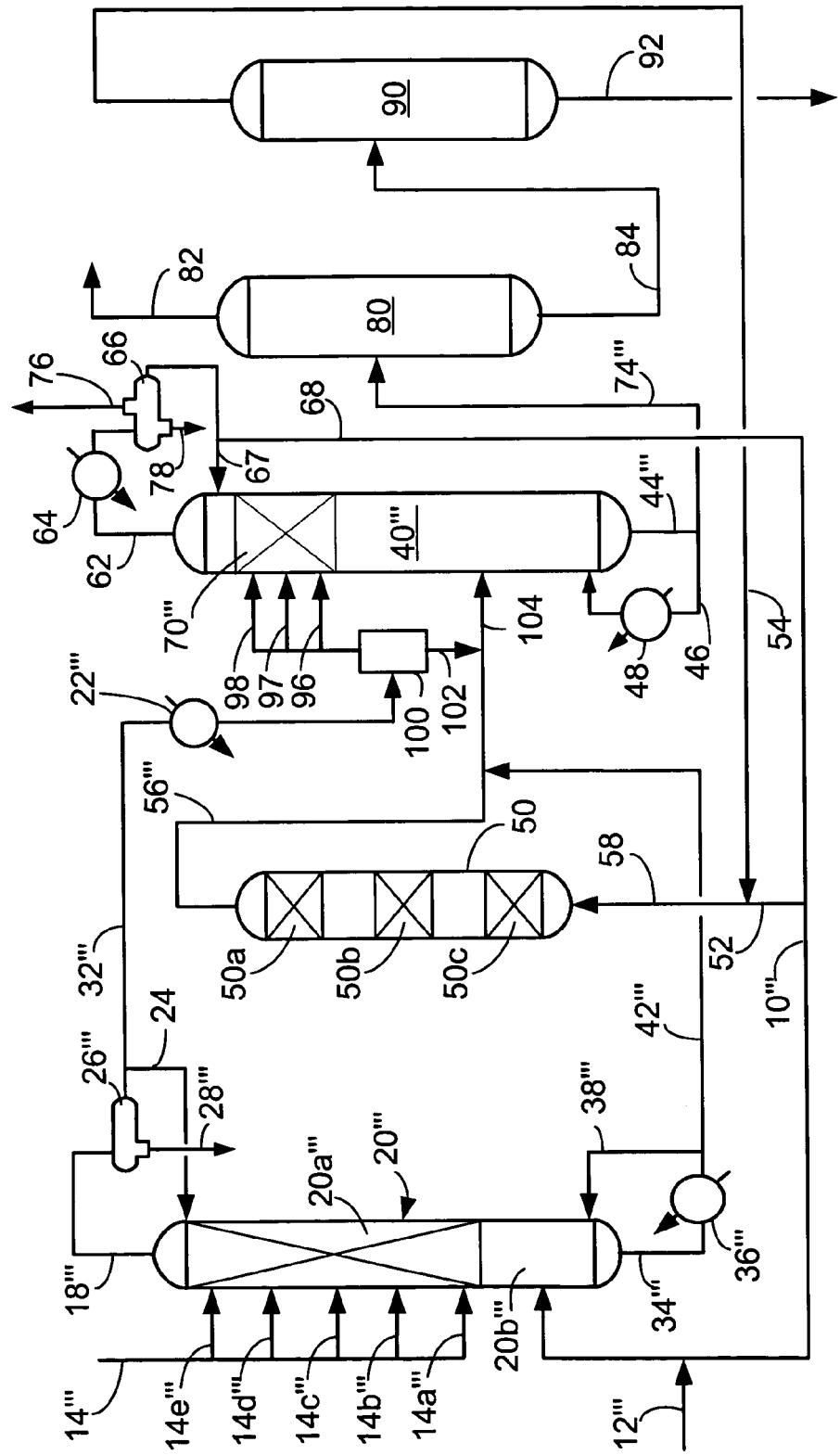
FIG. 6 depicts an alternative flow scheme of the present invention for the production of ethylbenzene.

FIG. 6 is a flow scheme for manufacturing ethylbenzene similar to FIGS. 1, 2 and 4, but using a catalytic distillation reactor 20''', an olefin recycle unit comprising a catalytic section 70''' in the benzene column 40''' and a flash drum 100. All of the reference numerals that designate an element in FIG. 6 which corresponds to a similar element in FIG. 1, 2 or 4 but which has a different configuration will be marked with a triple prime symbol ('''). Otherwise, the same reference numeral will designate corresponding elements in FIGS. 1, 2, 4 and 6 which have the same configuration.

A stream comprising ethylene enters the process in a line 14''' and is divided up in lines 14a'''-14e''' and delivered to a catalytic distillation alkylation reactor 20'''. The ethylene lines 14a'''-14e''' distribute ethylene at varying heights along the height of a catalytic section 20a''' of catalytic distillation alkylation reactor 20'''. Five lines 14a'''-14e''' are shown, but more or less may be used to distribute ethylene to different heights of the catalytic section 20*a'''*. Benzene is delivered to a lower, preferably non-catalytic section 20*b'''* of the catalytic distillation alkylation reactor 20'''. The catalytic distillation alkylation reactor 20''' is run at a temperature that will boil benzene upwardly at the column pressure in the catalytic distillation alkylation reactor 20''' to the catalytic section 20*a'''*. In the catalytic section 20*a'''*, the benzene and ethylene react over an alkylation catalyst secured therein as is known in the art to produce ethylbenzene which descends in the catalytic distillation alkylation reactor 20'''. The temperature of the catalytic section 20*a'''* will be in the range of about 60° C. to about 400° C. and the pressure will be in the range of about 0 to about 2758 kPa gauge. The alkylation conditions are operated to provide at least about 92% and preferably at least about 95% conversion of olefin, but less than full conversion and preferably no more than about 99.9% conversion of olefin. Alkylation bottom line 34''' removes ethylbenzene, polyethylbenzene and some benzene from the bottom of the catalytic distillation alkylation reactor 20'''. Reboiler 36''' heats the alkylation bottom stream in line 34''' and refluxes the alkylation bottom stream back to the lower section 20*b'''* of the catalytic distillation alkylation reactor 20'''. Line 42''' transports the remainder of the alkylation bottom stream to be mixed with a transalkylation effluent in line 56''' and flash drum bottoms in line 102 and delivers the mixture to the benzene column 40''' via line 104. Overhead stream in line 18''' is fed, without cooling to retain ethylene, to a preferably unvented receiver 26''' from which water is removed in line 28''' and a hydrocarbon product stream comprising some ethylbenzene, benzene, up to 8 mol-% ethylene based on the feed and inerts. The hydrocarbon product stream may be split between line 32''' and reflux line 24 which is refluxed back to the catalytic distillation alkylation reactor 20'''. Line 32''' carries the hydrocarbon product stream to an optional cooler 22''' and then to an optional flash drum 100. Otherwise, the line 32''' may feed the hydrocarbon product stream directly to the benzene column 40''' without cooling. The flash drum roughly separates ethylene and lights from ethylbenzene and heavier material which is removed from the flash drum 100 in line 102. The flash drum may be run at a temperature between about 180° C. and about 250° C. and preferably between about 200° C. and about 240° C. The pressure of the flash drum may be set between about 500 kPa gauge (73 psig) and about 1900 kPa gauge (276 psig). The operating pressure of the flash drum may be somewhat higher than the pressure in the benzene column 40''' to allow for convenient introduction of the vapor and liquid feed streams to the benzene column 40''' without additional compression or pumping. The pressure of the benzene column can vary but could be in the range of approximately 1400 kPa gauge (203 psig) to about 1800 kPa gauge (261 psig) in the catalytic section 70'''. The temperature of the catalytic section 70''' in the benzene column 40''' can vary but would be preferably be between 60° C. and about 400° C. Line 104 delivers benzene mixed with ethylbenzene and polyethylbenzene to a lower, preferably non-catalytic, section of the benzene column 40'''. Lines 96, 97 and 98 carry ethylene to different heights of catalytic section 70'''. Three lines 96, 97 and 98 are shown, but more or less may be used to distribute ethylene to different heights of the catalytic section 70'''.

Benzene from the line 68 is routed to the transalkylation reactor 50 through a line 52. The transalkylation is carried out as described with respect to FIG. 1. A line 54 carries a polyethylbenzene (PEB) column overhead stream of diethylbenzene (DEB) and triethylbenzene (TEB) from the overhead of a PEB column 90 to mix with the benzene in the line 52 to provide a transalkylation feed in a line 58. A transalkylation effluent stream in line 56 from the transalkylation reactor 50 contains a greater concentration of ethylbenzene and a lower concentration of DEB and TEB than in the transalkylation feed in line 58.

As shown in FIG. 6 with the alkylation and transalkylation reactors in parallel, the alkylation reactor effluent stream in the line 32''' carrying up to 8 mol-% ethylene relative to the feed, some inert lights, traces of water, benzene and ethylbenzene enters the benzene column 40. If it is desired to run the transalkylation reactor 50 and the catalytic distillation alkylation reactor 20''' in series, the effluent from the transalkylation reactor 50 is transported to the lower section 20*b'''* of the catalytic distillation alkylation reactor 20''' instead of being transported to the benzene column 40'''.

In the benzene column 40''', the ethylene is further separated from the ethylbenzene and heavier components and reacted over catalytic section 70'''. All of the ethylene reacts with benzene without concern over loss of ethylbenzene selectivity. A benzene column overhead stream comprising benzene, ethane and lights exits the benzene column through an overhead line 62 and enters a condenser 64 where it is cooled to a temperature between about 120° and about 170° C. The condensed overhead enters a receiver 66 which includes a trap for dispensing undissolved or free water in a line 78 and ethane and light gases exit in a line 76. A portion of the overhead hydrocarbon stream comprising mostly benzene is refluxed to the benzene column 40 via line 67 while the remaining benzene in line 68 is transported to the transalkylation reactor 50 via line 52 and to catalytic distillation alkylation reactor 20''' via line 10'''. A benzene column bottom stream comprising the product ethylbenzene and the by-products including PEBs exits the benzene column in a line 44'''. Line 74''' carries a portion of the benzene column bottoms from line 44''' to an ethylbenzene column 80, while line 46 carries reflux through reboiler 48 back to the benzene column. Further separation in the ethylbenzene column 80 and the polyethylbenzene column 90 are carried out as described with respect to FIG. 1.

Although several types of olefin recycle units are described with respect to each embodiment, each olefin recycle unit can be applied to any of the embodiments.

The invention will be further clarified by a consideration of the following examples, which are intended to be purely exemplary of the use of the invention.

EXAMPLES

Example I

We examined ethylbenzene yield as a function of ethylene conversion over a fixed bed for a number of catalysts. Catalyst A was a commercially made Beta zeolite supported on an alumina binder in weight proportions of 70/30, respectively. The Beta zeolite had a $Si/Al_2$ ratio of about 25. Catalyst A had been extruded, with a nominal particle diameter of 1/16 inches, dried and calcined in air at no more than 675° C. to provide an ABD of 0.58 g/ml. Catalyst B was a crystalline aluminosilicate designated UZM-8. The UZM-8 powder was synthesized according to the teachings of U.S. patent application Ser. No. 10/395,466. The powder was then acid washed according to the teachings of U.S. patent application Ser. No. 10/395,624. The UZM-8 was extruded with alumina support in weight proportions of zeolite to $Al_2O_3$ of 70/30, respectively. The extruded catalyst with a nominal particle diameter of 1/16 inches was calcined by first heating the catalyst up to 538° C. in an inert environment and then holding the temperature in air for 15 hours before cooling. The UZM-8 had a Si/Al$_2$ ratio of 47.5, and the finished Catalyst B had an ABD of 0.49 g/ml. Catalyst C is 50 wt-% Beta zeolite that was formed as an oil dropped sphere, dried, calcined, crushed and screened to obtain particles of 20×30 mesh. Catalyst D is the same material as Catalyst B, but the calcined extrudate was crushed and screened to obtain particles of 20×30 mesh. Data was generated in a pilot plant scale differential reactor at a pressure of 3,792 kPa gauge (550 psig). Feed to the reactor consisted of pure benzene and pure ethylene with a molar ratio of benzene to ethylene maintained at about 2.7 and the ethylene weight hourly space velocity was 1.98 hr$^{-1}$. For each test 4.40 grams of catalyst were loaded into the reactor along with sand to ensure good flow distribution. The total volume of catalyst and sand loaded into the reactor was 40 ml. The diluted bed was used to help control the exotherm in this once-through operation. The temperature was adjusted to provide varying ethylene conversions.

Figure 7:
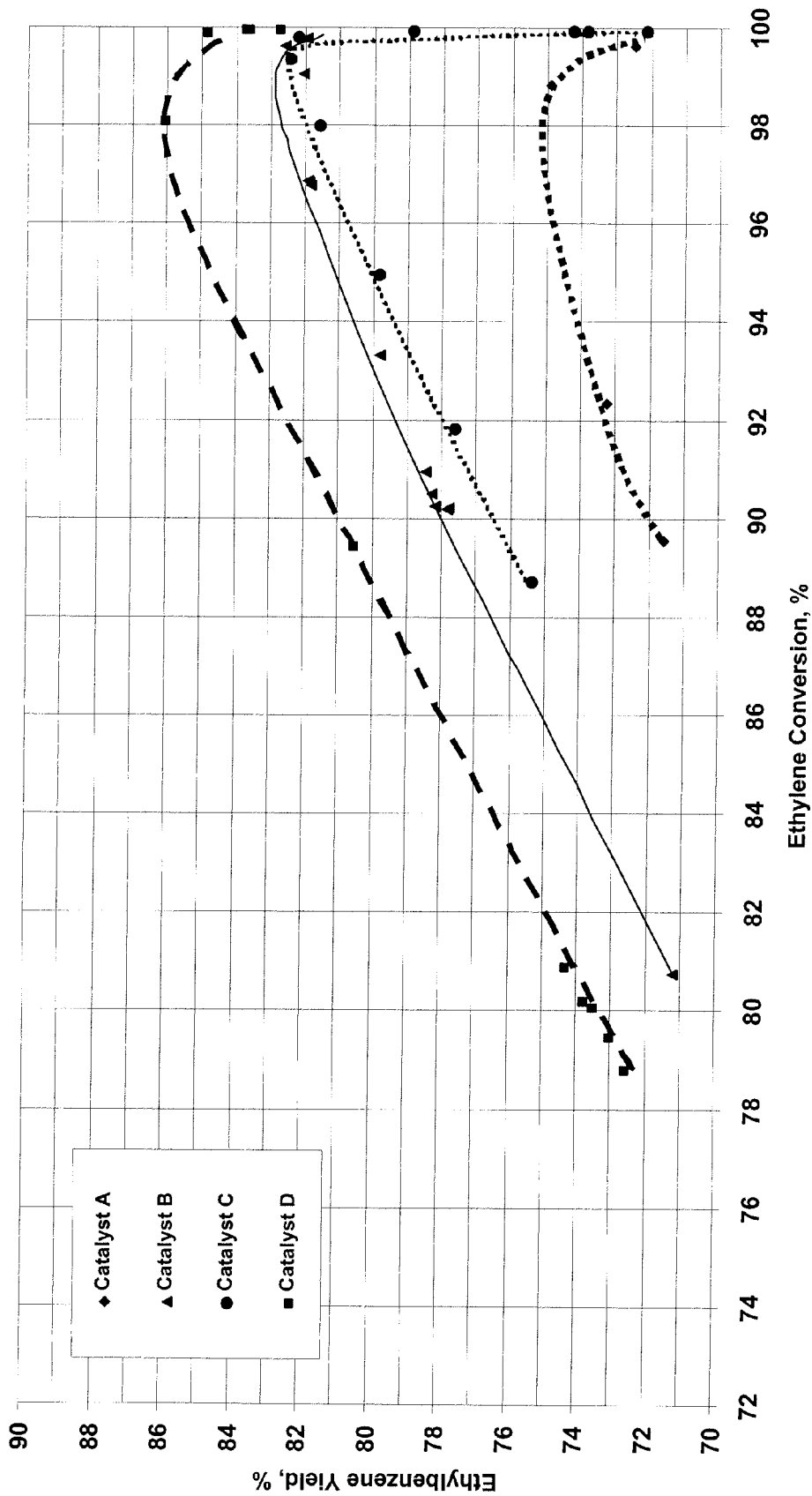
FIG. 7 depicts a plot of ethylbenzene yield versus ethylene conversion.

FIG. 7 shows the results for the tests. Ethylbenzene yield is equal to the product of ethylbenzene selectivity and ethylene conversion in the reactor effluent. Freeform lines illustrate the trends. The data shows that the ethylbenzene yield peaks between 97 and 99.5% and precipitously drops upon approaching 100% ethylene conversion. By controlling the ethylene conversion at greater than about 95% and less than 100%, an increase of 1 to 10% in ethylbenzene yield is possible. Monoalkylate aromatic yield at 99.9% olefin conversion was for some catalysts far superior to monoalkylate aromatic yield at olefin conversions approaching closer to 100%.

Figure 8:
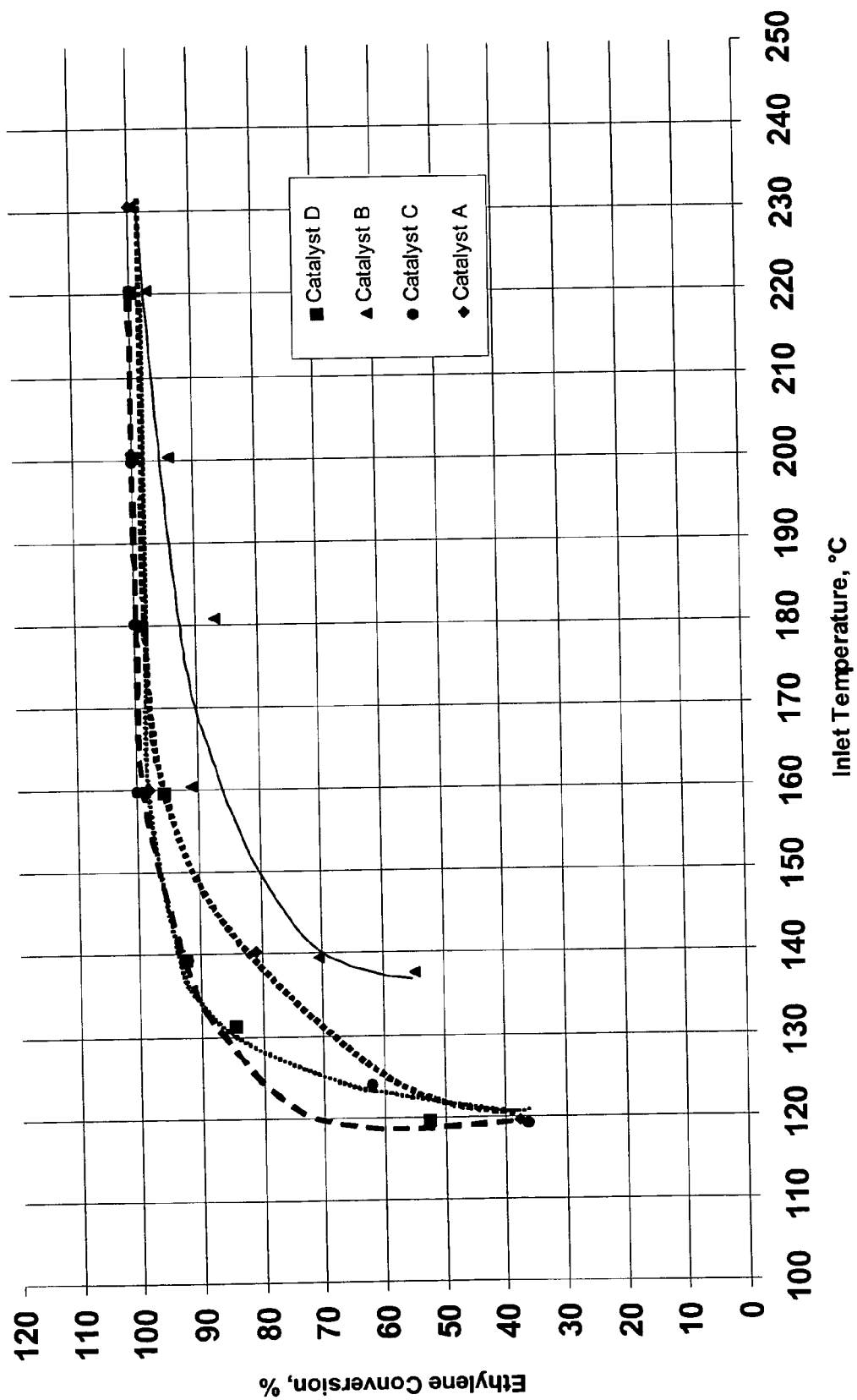
FIG. 8 depicts a plot of ethylene conversion versus reactor inlet temperature.

FIG. 8 shows olefin conversions as a function of the inlet temperature defined as the temperature at 5 cm (2 inches) upstream of the catalyst bed for each catalyst shown in FIG. 7.

Example II

We examined cumene yield as a function of propylene conversion in a batch operation. We used Catalyst A from Example I that had been crushed and screened to obtain catalyst particles of 20×40 mesh. Benzene and the catalyst were added to a batch reactor having a volume of 300 cm$^3$ and heated to an initial reaction temperature while stirring. Propylene was added to the catalyst and benzene mixture while samples of the reaction mixture were analyzed at intervals by gas chromatography. The sampling continued after termination of propylene addition. Residence time controlled propylene conversion.

Experiments were run under three different sets of conditions shown in Table A.

TABLE A

Experimental Conditions for Partial Propylene Conversion to Cumene

| Experiment | Catalyst-to-Olefin ratio | Benzene-to-Propylene ratio | Total Residence Time (minutes) | Initial Reaction Temperature (° C.) |
|---|---|---|---|---|
| E | 0.09 | 2.0 | 23.5 | 145 |
| F | 6.00 | 13.0 | 4.5 | 155 |
| G | 0.09 | 1.0 | 14.5 | 155 |

Figure 9:
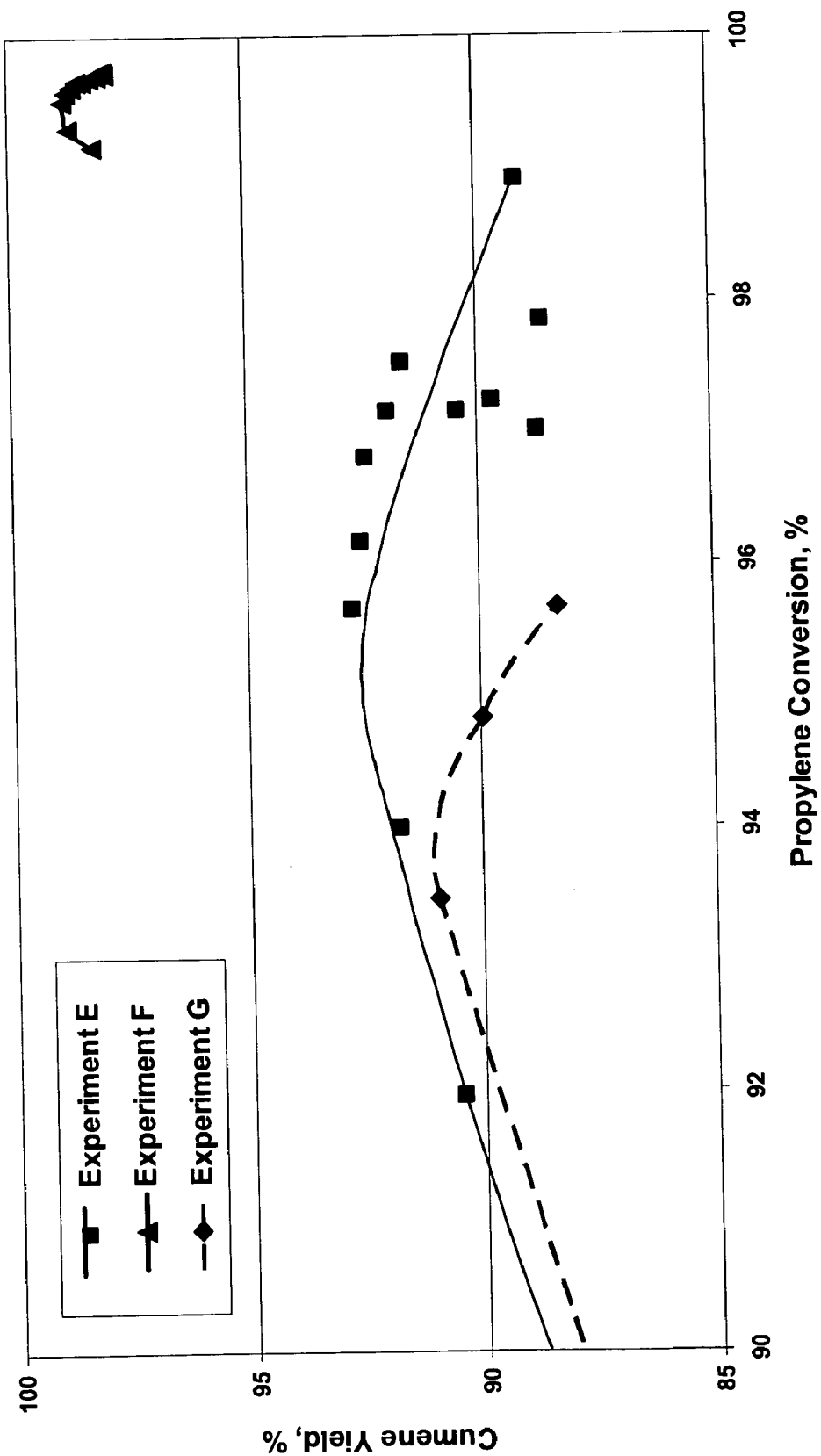
FIG. 9 depicts a plot of cumene yield versus propylene conversion.
Figure 10:
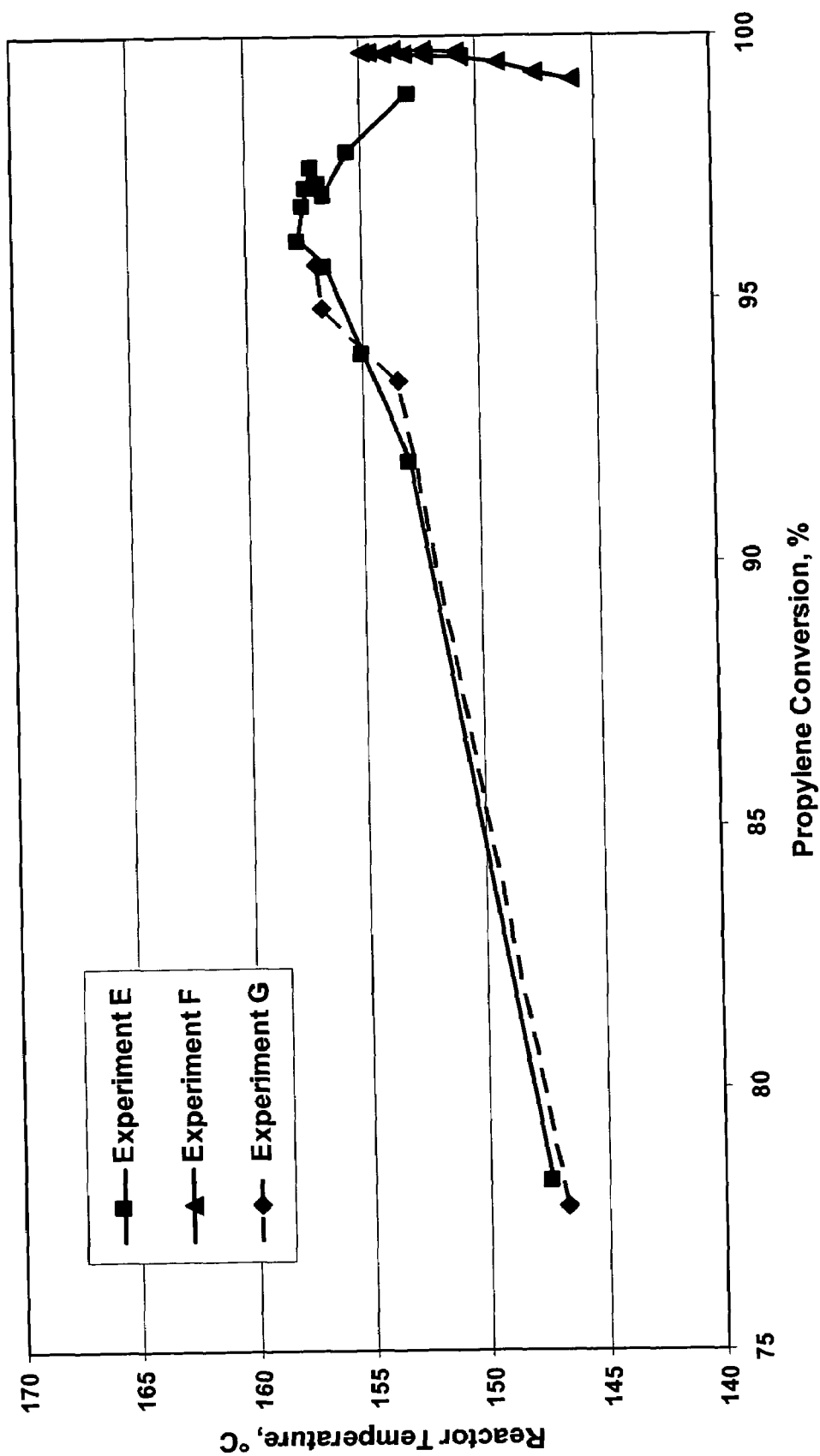
FIG. 10 depicts a plot of propylene conversion versus reactor inlet temperature.

The results of the experiments are shown in FIG. 9. Temperature data for each experiment is shown in FIG. 10.

The data shows that the cumene yield peaks between about 92 and 99.5% and drops upon approaching full propylene conversion. Freeform lines indicate the trends. By controlling the propylene conversion at greater than about 92% and less than 100%, an increase of 3 to 7% in cumene yield is possible under these experimental conditions depending on the benzene/propylene feed ratio. We believe that the advantages of increased monoalkylbenzene yield may be realized at as low as 92% olefin conversion. Monoalkylate aromatic yield at 99.5% olefin conversion was for one experiment far superior to monoalkylate aromatic yield at olefin conversions approaching closer to 100%.

What is claimed is:

1. A process for reacting an olefinic stream comprising ethylene with an aromatic stream comprising benzene to obtain an alkylaromatic product stream comprising ethylbenzene, the process comprising:

delivering the olefinic stream to a reactor vessel containing an alkylation catalyst comprising at least one of beta zeolite and UZM-8 zeolite;

delivering the aromatic stream to said reactor vessel;

contacting ethylene in said olefinic stream and benzene in said aromatic stream with said alkylation catalyst to obtain alkylaromatics comprising ethylbenzene under alkylation conditions including a conversion of ethylene in said olefinic stream ranging from at least 97% to no more than 99.5%; and recovering the alkylaromatic product stream comprising ethylbenzene.

2. The process of claim 1 further including transporting a reactor effluent stream comprising unconverted olefins and aromatics to a separation vessel.

3. The process of claim 2 further including separating unconverted olefins from alkylaromatics in said separation vessel.

4. The process of claim 1 wherein unconverted olefins comprise at least 0.1% of said alkylaromatic product stream on a fresh feed basis.

5. The process of claim 2 further including recovering separated unconverted olefins.

6. The process of claim 1 further including recovering unconverted olefins in a gaseous phase, pressurizing the unconverted olefins and recycling the unconverted olefins back to the reactor vessel.

7. The process of claim 1 further including contacting the unconverted olefins with an aromatics stream over an alkylation catalyst in a finishing reactor.

8. The process of claim 2 further including recycling unconverted olefins to said reactor vessel.

9. The process of claim 8 wherein the unconverted olefins are recycled back to the reactor vessel in an aromatics stream.

10. The process of claim 2 wherein the separator vessel includes a catalytic section in which said unconverted olefins are alkylated with aromatics.

11. The process of claim 3 wherein unconverted olefins from the separator vessel are transported to a catalytic separator vessel.

12. The process of claim 1 wherein unconverted olefins comprise at least 0.5% of the reactor effluent stream on a fresh feed basis.

13. The process of claim 3 further comprising directing unconverted olefins to an olefin recycle unit.

* * * * *

UNITED STATES PATENT AND TRADEMARK OFFICE
CERTIFICATE OF CORRECTION

PATENT NO. : 7,622,622 B1  
APPLICATION NO. : 10/872615  
DATED : November 24, 2009  
INVENTOR(S) : Woodle et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 151 days.

Signed and Sealed this

Twenty-sixth Day of October, 2010

David J. Kappos
*Director of the United States Patent and Trademark Office*